United States Patent

Umezawa et al.

[11] 4,337,336
[45] Jun. 29, 1982

[54] DERIVATIVE OF KANAMYCIN A AND A PROCESS FOR THE PREPARATION THEREOF

[75] Inventors: Hamao Umezawa; Sumio Umezawa; Shunzo Fukatsu, all of Tokyo; Toshio Yoneta; Tadashi Wakazawa, both of Yokohama, all of Japan

[73] Assignee: Zaidan Hojin Biseibutsu Kagaku Kenkyu Kai, Tokyo, Japan

[21] Appl. No.: 235,576

[22] Filed: Feb. 18, 1981

[30] Foreign Application Priority Data

Feb. 25, 1980 [JP] Japan .................................. 55/21666

[51] Int. Cl.³ .................... A61K 31/71; C07H 15/22
[52] U.S. Cl. .................................. 536/13.8; 424/180
[58] Field of Search ........................... 536/10, 17 R

[56] References Cited

U.S. PATENT DOCUMENTS

Re. 28,647  12/1975  Umezawa et al. ............... 536/10
4,060,682   11/1977  Umezawa et al. ............... 536/10
4,078,138    3/1978  Akita et al. ................... 536/10
4,195,170    3/1980  Umezawa et al. ............... 536/10

Primary Examiner—Johnnie R. Brown
Attorney, Agent, or Firm—Larson and Taylor

[57] ABSTRACT

There are provided new compounds, 3',4'-anhydro-4'-epi derivatives of kanamycin A of the formula:

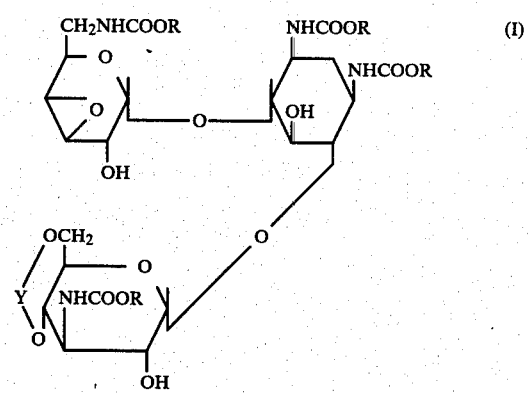

wherein R represents an alkyl, aralkyl or aryl group and Y represents an alkylidene, aralkylidene, cycloalkylidene or tetrahydropyranylidene group which are useful as an intermediate for the synthesis of 3',4'-dideoxykanamycin A and 4'-deoxykanamycin A from kanamycin A. The compounds of formula (I) can be prepared by treating the corresponding 4'-O-sulfonyl derivative with an alkali metal alcoholate in a lower alkanol under an alkaline condition.

6 Claims, No Drawings

DERIVATIVE OF KANAMYCIN A AND A PROCESS FOR THE PREPARATION THEREOF

BRIEF SUMMARY OF THE INVENTION

This invention relates to a 3',4'-anhydro-4'-epi derivative of kanamycin A and its preparation from kanamycin A.

The 3',4'-anhydro-4'-epi derivative is a new and useful intermediate for the synthesis of deoxy derivatives of kanamycin A which are active against a variety of kanamycin A-resistant strains of bacteria.

According to this invention, there is provided a 3',4'-anhydro-4'-epi derivative of kanamycin A of formula (I):

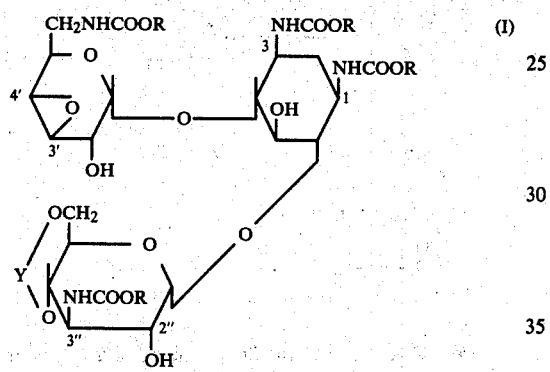

wherein R represents an alkyl, aralkyl or aryl group and Y represents an alkylidene, aralkylidene, cycloalkylidene or tetrahydropyranylidene group.

In the compounds of formula (I), the group -COOR is a known amino-protecting group of urethane type, in which R is preferably an alkyl of 1–6 carbon atoms, benzyl, phenyl or a substituted phenyl such as nitrophenyl. The group Y may be a known hydroxyl-protecting divalent group as defined above and preferably is a lower alkylidene such as formylidene, ethylidene and isopropylidene; a phenylalkylidene such as benzylidene; cyclopentylidene and cyclohexylidene; and tetrahydropyranylidene group.

The compounds of formula (I) are useful intermediates for the preparation of 3',4'-dideoxykanamycin A of formula (III) or 4'-deoxykanamycin A of formula (IV), as it is easily convertible to the compound of formula (III) or (IV) by the 3',4'-epoxide ring opening with a nucleophile such as a halogen and a suitable treatment of the derived halogenohydrin derivative followed by the removal of the amino- and hydroxyl-protecting groups.

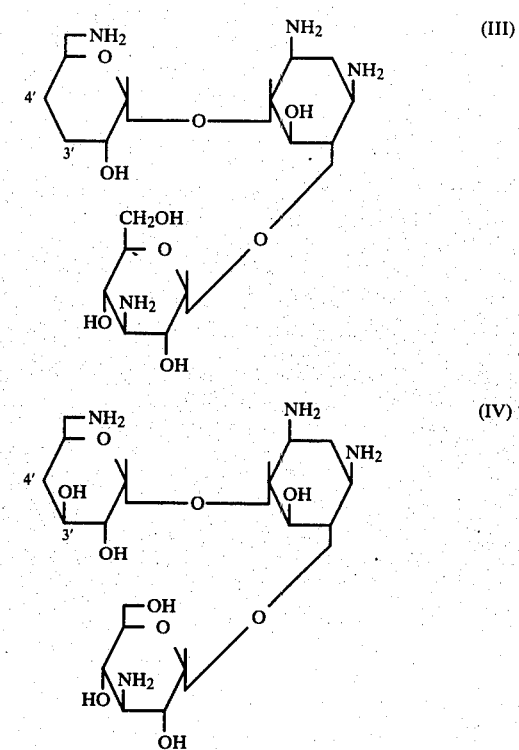

BACKGROUND OF THE INVENTION

3',4'-Dideoxykanamycin A of formula (III), which was first prepared semi-synthetically from kanamycin A by H. Umezawa et al. (Japanese Patent KOKAI No. 105699/80; Belgian Pat. No. 881251; U.S. Pat. No. 4,195,170; U.S. patent application Ser. No. 187,014), and 4'-deoxykanamycin A of formula (IV), which was first prepared semi-synthetically from kanamycin A by Naito et al. (Japanese Patent KOKAI No. 93944/75; U.S. Pat. No. 3,886,138), are known to exhibit an improved anti-bacterial activity against kanamycin-sensitive and -resistant organisms, as compared with kanamycin A. However, both the methods referred to above require many steps to obtain suitably protected derivatives of kanamycin A which possess only the objective hydroxyl group free. In both the methods, it was necessary, in order to obtain the protected kanamycin A derivatives containing the free 4'-hydroxyl group, to take complicated preparatory steps. Thus the 6'-amino group of kanamycin A was protected with an amino-protecting group and the other amino groups were protected with another protecting group. After the formation of 4',6'-O,N-cyclic carbamate with a base, the hydroxyl groups which are not to be removed were protected with a hydroxyl-protecting group. After the subsequent ring-opening of the carbamate, the 6'-amino group was again protected with an amino-protecting group.

General deoxygenation procedure, which is elegantly applied for the preparation of 3',4'-dideoxykanamycin B and tobramycin from kanamycin B via their sulfonyl derivatives, is not suitable for kanamycin A derivative because the protecting steps prior to the deoxygenation are very complicated.

We have investigated the application of the new process proposed by use for the preparation of 3',4'-dideoxykanamycin B (Japanese Patent KOKAI No. 71445/77; U.K. Pat. No. 1,537,905) to the preparation of deoxy derivatives of kanamycin A. The process disclosed in this publication is based on taking advantage of a behavior of saccharide in an acylation reaction that the reactivity of the 4-hydroxyl group is markedly lower than that of any other hydroxyl group thereof and comprises reacting 4'',6''-O-protected derivative of penta-N-protected kanamycin B with an alkanoyl chloride or aroyl chloride, typically benzoyl chloride, in pyridine to acylate the 3'- and 2''-hydroxyl groups to leave the 4'-hydroxyl group free. Sulfonylation of the 4'-hydroxyl group of the acylated derivative gives a compound of formula (V):

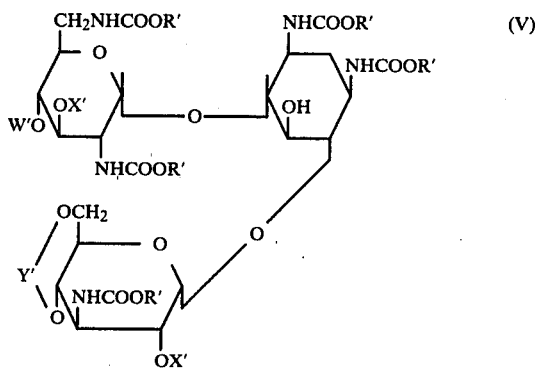
(V)

wherein R' represents an alkyl or aryl group; W' represents a mesyl, tosyl or benzylsulfonyl; X' represents an alkanoyl group, typically those containing 2–4 carbon atoms such as acetyl or an aroyl group, typically benzoyl; and Y' represents an alkylidene, aralkylidene, cycloalkylidene or tetrahydropyranylidene group. Treatment of the resulting compound with an alkali metal alcoholate in a lower alkanol under alkaline conditions affords the 3',4'-anhydro-4'-epi derivative of kanamycin B of formula (VI):

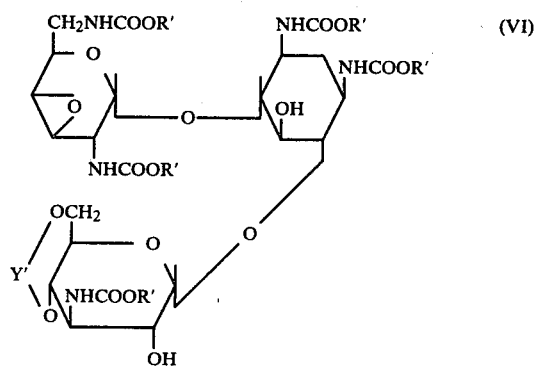
(VI)

wherein R' and Y' have the same meanings as defined above, as an intermediate with a high yield in a relatively small number of steps.

The difference in chemical structure between kanamycin B and kanamycin A resides in that the former has an amino group in the 2'-position, whereas the latter has a hydroxyl group in that position. We have now found that kanamycin A can be converted to 3',4'-anhydro-4'-epi derivative by the following method. Firstly, all the four amino groups of kanamycin A are protected with an amino-protecting group. After the reaction of the tetra-N-protected kanamycin A with a divatent hydroxyl-protecting reagent, the resulting 4'',6''-O-protected derivative is treated with an alkanoyl halide or aroyl halide, typically benzoyl halide, to acylate the 2'-, 3'- and 2''-hydroxyl groups and to leave the 4'-hydroxyl group free without acylation, followed by the sulfonylation of the 4'-hydroxyl group and the treatment of the sulfonylated derivative thus formed with an alkali metal alcoholate in an alkanol. The resulting 3',4'-anhydro-4'-epi derivative can be converted to 3',4'-dideoxykanamycin A in a manner known per se.

DETAILED EXPLANATION OF THE INVENTION

According to a further aspect of this invention, therefore, there is provided a process for the preparation of 3',4'-anhydro-4'-epi derivative of kanamycin A of formula (I):

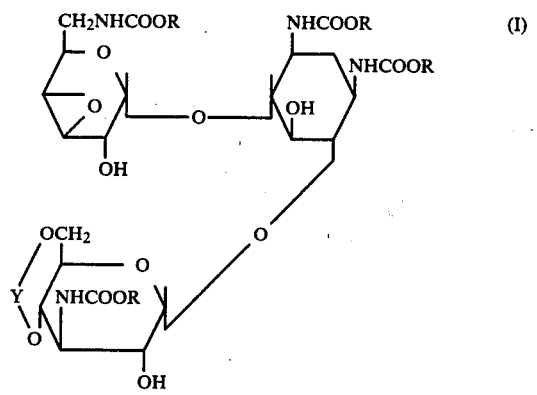
(I)

wherein R represents an alkyl, aralkyl or aryl group and Y represents an alkylidene, aralkylidene, cycloalkylidene or tetrahydropyranylidene group which comprises treating a 4'-O-sulfonyl derivative of kanamycin A of formula (II):

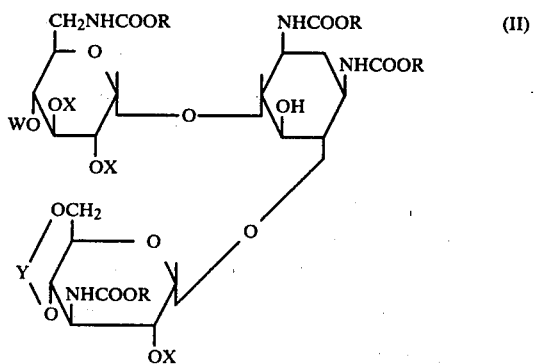
(II)

wherein R and Y have the same meanings as defined above, W represents a mesyl, tosyl or benzylsulfonyl group and X represents an alkanoyl or aroyl group with an alkali metal alcoholate in a lower alkanol under an alkaline condition.

In practicing the process of this invention, kanamycin A is first treated to protect the four amino groups thereof in the form of a urethane-type group in a known manner per se, thus giving a tetra-N-protected derivative of kanamycin A of formula (VII):

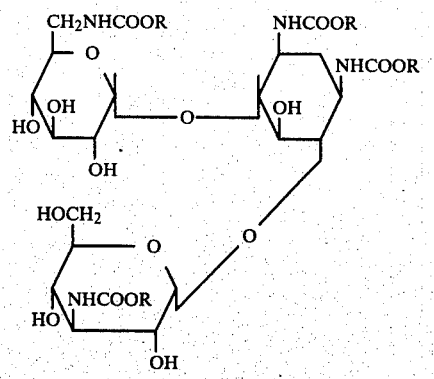

(VII)

wherein R has the same meaning as defined above. The compound of formula (VII) is then treated to protect selectively the 4''- and 6''-hydroxyl groups by reacting it with an alkylidenylating agent, an aralkylidenylating agent, a cycloalkylidenylating agent or a tetrahydropyranylidenylating agent as a known hydroxyl-protecting agent. The reaction may preferably be effected by treating the compound of formula (VII) with a hydroxyl-protecting agent in a solvent such as dimethylformamide in the presence of a catalytic amount of p-toluene sulfonic acid at room temperature, usually 15°–25° C. for 15–20 hours, the hydroxyl-protecting agent being a known alkylidenylating or aralkylidenylating agent such as acetaldehyde, 2,2-dimethoxypropane, anisaldehyde, benzaldehyde and diethylacetal or a known cycloalkylidenylating agent such as 1,1-dimethoxycyclohexane or a known tetrahydropyranylidenylating agent such as 1,1-dimethoxytetrahydropyranylidene. The amino-protecting and hydroxyl-protecting steps above-mentioned may be carried out in the same manner as that described in Japanese Patent KOKAI No. 71445/77 or U.K. Pat. No. 1,537,905. Thus, there is formed a 4'',6''-O-protected derivative of formula (VIII):

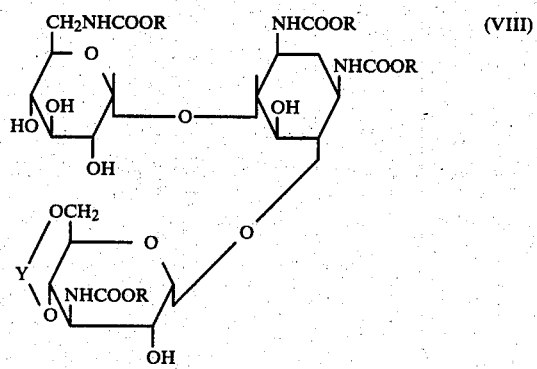

(VIII)

wherein R and Y have the same meanings as defined above. The compound of formula (VIII) is treated to protect selectively the 2'-, 3'- and 2''-hydroxyl groups with an hydroxyl-protecting group of acyl type. This step may usually be conducted by reacting the compound of formula (VIII) with an acylating agent such as an acyl chloride in pyridine at a low temperature, particularly below 5° C. As the acylating agent, there may be used an acid chloride of a suitable carboxylic acid, particularly an alkanoic acid having 2–4 carbon atoms such as acetyl chloride and benzoyl chloride. Benzoyl chloride is a preferred acylating agent for this step. Since the 4'-hydroxyl group is not acylated in this step, there is formed a 2',3',2''-tri-O-acyl derivative of formula (IX):

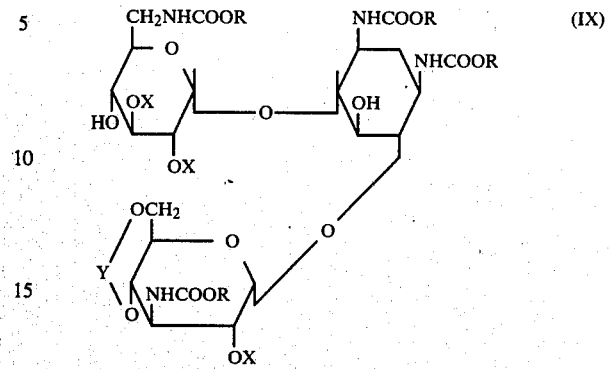

(IX)

wherein R and Y have the same meanings as defined above and X represents an acyl group, for example a lower alkanoyl such as acetyl or an aroyl such as benzoyl.

The next step is a sulfonylation of the 4'-hydroxyl group of the compound of formula (IX). Thus, the 4'-O-sulfonylation may be carried out by reacting the compound of formula (IX) with mesyl chloride, tosyl chloride or benzylsulfonyl chloride in pyridine. The reaction temperature may be within the range of 20° to 50° C. Mesyl chloride is preferred as the 4'-O-sulfonylating agent. Thus, there is formed a 4'-O-sulfonylated derivative of formula (II):

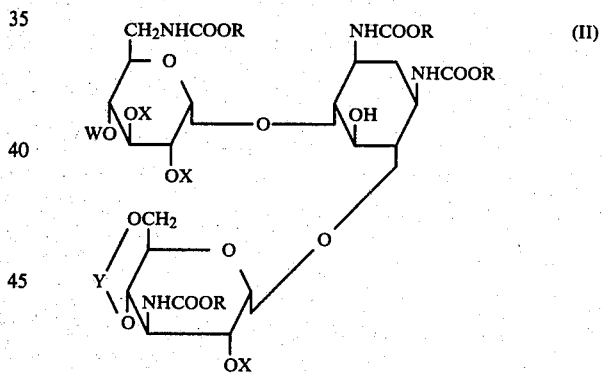

(II)

wherein R, X and Y have the same meanings as defined above and W represents a mesyl, tosyl or benzylsulfonyl group, which is used as starting compound in the process according to this invention.

In the process of this invention, the compound of formula (II) is 3',4'-epoxidized. The 3',4'-epoxidation may be carried out by dissolving the compound of formula (II) in a lower alkanol of 1–4 carbon atoms as methanol and ethanol and treating it in the solution with an alkali metal, e.g. sodium or potassium, alcoholate, particularly a lower alkoxide such as methoxide or ethoxide. The use of sodium methoxide or sodium ethoxide is preferred. Suitably, the 3',4'-epoxidation may be conducted at room temperature, usually 15°–20° C. for 1–3 hours. Thus, there is formed a protected derivative of 3',4'-anhydro-4'-epi-kanamycin A of formula (I):

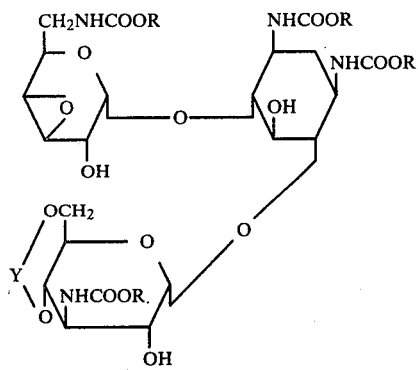

wherein R and Y have the same meanings as defined above with a simultaneous hydrolytic elimination of the 2'- and 2''-acyl groups (X).

The compounds of formula (I) according to this invention can be converted to 3',4'-dideoxykanamycin A in the same manner as that described in Japanese Patent KOKAI No. 71445/77 or U.K. Patent No. 1,537,905 above-referred to by treating the compound of formula (I) with a xanthate to form a protected derivative of 3',4'-dideoxy-3',4'-didehydrokanamycin A, i.e. 3',4'-dideoxy-3'-enokanamycin A of formula (X):

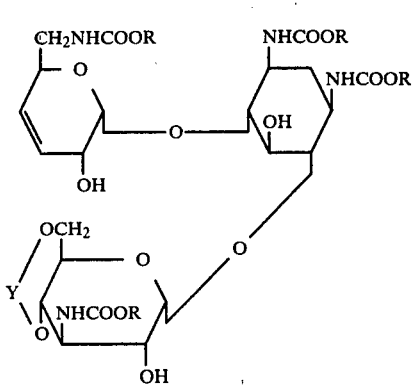

wherein R and Y have the same meanings as defined above, removing the amino-protecting and hydroxyl-protecting groups and then hydrogenating the 3',4'-unsaturation.

There is an alternative process for the conversion of the compound of formula (I) to 3',4'-dideoxykanamycin A which comprises the steps of protecting the 2'- and 2''-hydroxyl groups of the compound of formula (I) with an acyl chloride, particularly an aroyl chloride such as benzoyl chloride in pyridine, treating the 2',2''-di-O-acyl derivative thus formed with sodium iodide, sodium acetate and acetic acid in acetone in accordance with the process described in "Bull. Chem. Soc. Japan", 52, No. 4, 1131–1134 (1979) to give an iodohydrin derivative of formula (XI):

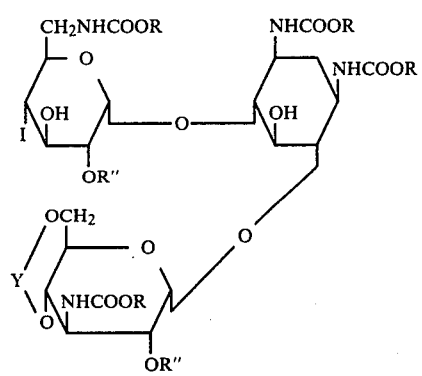

wherein R and Y have the same meanings as defined above and R'' represents an acyl group, treating the resulting compound with benzylsulfonyl chloride in pyridine, heating the resulting benzylsulfonyloxy derivative at 90° C. for 20–30 minutes to form the corresponding 3'-ene derivative, removing the amino-protecting and hydroxyl-protecting groups to give 3'-ene-kanamycin A and finally hydrogenating the resulting compound to form 3',4'-dideoxykanamycin A. 4'-Deoxykanamycin A can be obtained by hydrogenating the iodohydrin derivative in the presence of Raney nickel catalyst and then removing the amino-protecting and hydroxyl-protecting groups in a known manner.

According to a further aspect of this invention, there is provided a process for the preparation of an iodohydrin derivative of N,O-protected kanamycin A of formula (XI):

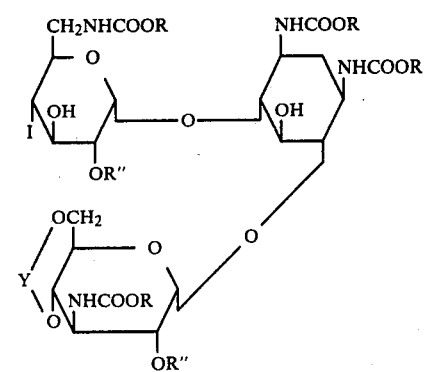

wherein R represents an alkyl, aralkyl or aryl group, Y represents an alkylidene, aralkylidene, cycloalkylidene or tetrahydropyranylidene group, and R'' represents an acyl group, particularly an aroyl group, which comprises reacting a 3',4'-anhydro-4'-epi derivative of N,O-protected kanamycin A of formula (I):

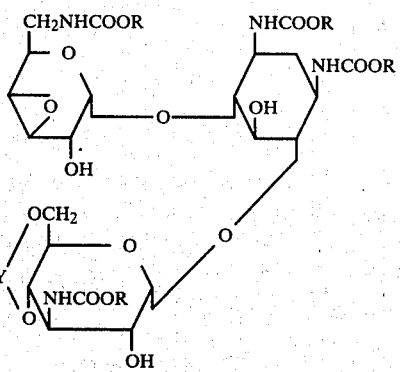

(I)

wherein R and Y have the same meanings as defined above, with an acyl chloride, particularly an aroyl chloride, in pyridine to form the corresponding 2',2"-di-O-acylated derivative, and then treating the 2',2"-di-O-acylated derivative with sodium iodide, sodium acetate and acetic acid in acetone.

By ulitizing the process according to this invention, therefore, there is established a new route for the preparation of 3',4'-dideoxykanamycin A and 4'-deoxykanamycin A from kanamycin A through the compound of formula (II) and the compound of formula (I). This process can reduce the reaction steps up to the preparation of the intermediate compound of formula (I) as compared with the prior art processes and is thus advantageous particularly in an industrial operation.

PREFERRED EMBODIMENT OF THE INVENTION

This invention is further illustrated by the following Example in which the overall steps for the preparation of 3',4'-dideoxykanamycin A or 4'-deoxykanamycin A starting from kanamycin A are given.

EXAMPLE (1) Preparation of tetra-N-t-butoxycarbonylkanamycin A

To a solution of kanamycin A monosulfate (17.5 g) and sodium hydroxide (2.4 g) in a mixture of water (120 ml), triethylamine (36 ml) and dioxane (200 ml), was added under stirring t-butyl-S-(4,6-dimethyl-pyrimidin-2-yl)-thiolcarbonate (43.2 g) as t-butoxycarbonyl group-introducing reagent and the resulting mixture was stirred overnight at room temperature. A precipitated mass thus formed was washed with 1 N-hydrochloric acid and then water and dried, yielding 20 g (75%) of the titled compound. $[\alpha]_D^{25} +74.1°$ (c=1.0, dimethylformamide).

Elemental analysis: Found: C, 50.92; H, 7.58; N, 6.45%: Calculated for $C_{38}H_{68}N_4O_{19}$: C, 51.56; H, 7.76; N, 6.33%

(2) Preparation of 4",6"-O-cyclohexylidene-tetra-N-t-butoxycarbonylkanamycin A

The compound obtained in the step (1) above (10.5 g) was dissolved in dimethylformamide (200 ml), to which were then added 1,1-dimethoxycyclohexane (20 ml) and p-toluenesulfonic acid monohydrate (0.4 g) and the resulting mixture was stirred at room temperature for 18 hours. The reaction mixture was neutralized with triethylamine, concentrated under vacuum and then poured into water (200 ml). A precipitate thus deposited was filtered, washed with water and dried to yield 11 g (96%) of the titled compound. $[\alpha]_D^{25} +67.0°$ (c=1.0, pyridine).

Elemental analysis: Found: C, 53.82; H, 7.41; N, 5.25%: Calculated for $C_{44}H_{76}N_4O_{19}$: C, 54.25; H, 7.95; N, 5.81%:

(3) Preparation of 2',3',2"-tri-O-benzoyl-4",6"-O-cyclohexylidene-tetra-N-t-butoxycarbonylkanamycin A The compound obtained in the step (2) above (11.4 g) was dissolved in pyridine (200 ml). After the solution was cooled to 0°–5° C., benzoyl chloride (5.6 ml) was added to the solution and the reaction was conducted for 3 hours at 0°–5° C. The completion of reaction was confirmed by thin layer chromatography [silica gel, Merck & Co.]. Then, water (5 ml) was added to the reaction mixture to decompose any excess of the benzoyl chloride used. After the reaction mixture was concentrated, it was poured into water (300 ml) and a precipitate thus deposited was filtered, washed well with a 1 N aqueous sodium hydrogen carbonate, then with water and dried to yield 14.8 g of a crude product. This was purified by a silica gel chromatography to yield 10.2 g (75%) of the titled compound. $[\alpha]_D^{25} +100.5°$ (c=1.1, chloroform), m.p. 182°–188° C.

Elemental analysis: Found: C, 60.31; H, 6.74; N, 4.09%: Calculated for $C_{65}H_{88}N_4O_{22}$: C, 61.10; H, 6.96; N, 4.39%.

(4) Preparation of 2',3',2"-tri-O-benzoyl-4",6"-O-cyclohexylidene-4'-O-mesyl-tetra-N-t-butoxycarbonylkanamycin A The compound obtained in the step (3) above (1.9 g) was dissolved in pyridine (30 ml), to which was then added mesyl chloride (0.4 ml) and the reaction was conducted at room temperature for 3 hours. Water (0.2 ml) was added to the reaction mixture to decompose any excess of the mesyl chloride used. After the reaction mixture was concentrated, it was poured into water (50 ml) and a precipitate thus formed was filtered, washed with water and dried to yield 2.0 g (quantitative) of the titled compound. $[\alpha]_D^{25} +103.3°$ (c=1.0, chloroform), m.p. 194°–204° C. (with decomposition).

Elemental analysis: Found: C, 58.45; H, 6.52; N, 4.23; S, 2.20%: Calculated for $C_{66}H_{90}N_4O_{24}S$: C, 58.47; H, 6.71; N, 4.13; S, 2.36%.

(5) Preparation of 3',4'-anhydro-4'-epi-4",6"-O-cyclohexylidene-tetra-N-t-butoxycarbonylkanamycin A This step is the process according to this invention.

The compound obtained in the step (4) above (5.1 g) was dissolved in methanol (100 ml), to which sodium methylate (1.2 g) was added and the mixture was stirred at room temperature for 2 hours to conduct the reaction. The reaction mixture was neutralized with concentrated hydrochloric acid under ice-cooling, concentrated and poured into water (200 ml). The resulting precipitate was filtered, washed with water and dried to yield 3.1 g (88%) of a crude product. This was purified by silica gel chromatography to afford the titled compound with the following properties. $[\alpha]_D^{25} +54.1°$ (c=1.0, dimethylformamide), m.p. 190°–207° C. (with decomposition).

Elemental analysis: Found: C, 52.14; H, 7.60; N, 6.15%: Calculated for $C_{38}H_{66}N_4O_{18}$: C, 52.63; H, 7.69; N, 6.46%.

(6) Preparation of 3',4'-anhydro-4'-epi-2',2''-di-O-benzoyl-4'',6''-O-cyclohexylidene-tetra-N-t-butoxycarbonylkanamycin A and subsequent ring-opening for the formation of the corresponding 3'-hydroxy-4'-deoxy-4'-iodo, i.e. iodohydrin, derivative The compound obtained in the step (5) above (4.3 g) was dissolved in pyridine (45 ml), to which benzoyl chloride (3 ml) was added and the reaction was conducted at room temperature for 2 hours. Water (1 ml) was added to the reaction mixture to decompose the excess of benzoyl chloride, after which the reaction mixture was concentrated and poured into water (100 ml). The resulting precipitate was filtered, washed with 1 N aqueous sodium hydrogen carbonate, water, and dried. The dried product, without being purified, was dissolved in acetone (4.5 ml), to which were then added acetic acid (3.3 ml), sodium acetate (0.2 g) and sodium iodide (5.8 g) and the reaction was conducted under reflux for 4 hours. The reaction mixture was allowed to cool to room temperature, concentrated and poured into water (200 ml). A precipitated mass was filtered, washed with water and dried to yield 5.5 g of a crude product. This was purified by silica gel chromatography to afford 3.9 g (71%) of the titled iodohydrin derivative.

Elemental analysis: Found: I, 9.31%: Calculated for $C_{52}H_{75}N_4O_{20}I$: I, 9.84%.

(7) Preparation of 2',2''-di-O-benzoyl-4'',6''-O-cyclohexylidene-3'-eno-tetra-N-t-butoxycarbonylkanamycin A The compound obtained in the step (6) above (2.6 g) was dissolved in pyridine (50 ml) and the solution was ice-cooled, to which benzylsulfonyl chloride (1.5 g) was added and the reaction was conducted for 1 hour under ice-cooling. Water (0.5 ml) was added to decompose the excess of benzylsulfonyl chloride used and the reaction mixture was treated at 90° C. for 1 hour, allowed to cool to room temperature, concentrated and then poured into water (200 ml). The resulting precipitate was filtered, washed with water and dried to yield 2.1 g of a crude product. This was purified by silica gel chromatography to afford 1.3 g (56%) of the titled compound. $[\alpha]_D^{25}$ +19.1° (c=1.0, chloroform), m.p. 221°–226° C. (with decomposition).

Elemental analysis: Found: C, 61.78; H, 7.31; N, 4.45%: Calculated for $C_{58}H_{82}N_4O_{19}$: C, 61.13; H, 7.27; N, 4.92%.

(8) Preparation of 3'-eno-kanamycin A

To a solution of the compound obtained in the step (7) above (1.1 g) in methanol (20 ml), was added sodium methoxide (0.3 g). The reaction was conducted at room temperature for 1 hour and then at 50° C. for 2 hours with the addition of 6 N hydrochloric acid (5 ml). The reaction mixture was neutralized with 2 N aqueous sodium hydroxide under ice-cooling, concentrated, dissolved in water (50 ml) and adsorbed on a column of 30 ml of Amberlite CG-50(NH4+) (Amberlite is registered trade mark for ion-exchange resins sold by Rohm & Hass Co.). Chromatographic purification was effected with 0.3 N aqueous ammonia as eluent, yielding 0.34 g (75%) of the titled compound $[\alpha]_D^{25}$ +52.1 (c=1.0, water).

Elemental analysis: Found: C, 44.36; H, 7.21; N, 10.54%: Calculated for $C_{18}H_{34}N_4O_9 \cdot H_2CO_3$: C, 44.51; H, 7.09; N, 10.93%.

(9) Preparation of 3',4'-dideoxykanamycin A

3'-Eno-kanamycin A obtained in the step (8) above (200 mg) was dissolved in water (100 ml). Platinum oxide (15 mg) was added to the solution and hydrogen was passed through the solution at room temperature under atmospheric pressure for 2 hours. The catalyst was removed by filtration to yield 185 mg of 3',4'-dideoxykanamycin A.

(10) Preparation of 4'-deoxykanamycin A

The iodohydrin derivative obtained in the step (6) above (550 mg) was dissolved in methanol (10 ml), to which were then added dioxane (10 ml) and water (5 ml). Raney nickel (2.3 g) was added to the solution to cause the reduction reaction under atmospheric pressure. After the catalyst was removed by filtration, sodium methylate (60 mg) was added to the reaction solution and the mixture was allowed to stand at room temperature for 2 hours, then neutralized with 1 N hydrochloric acid and concentrated to dryness. The residue was washed with water and added to 95% trifluoroacetic acid (4.5 ml) and the mixture was allowed to stand at room temperature for 30 minutes. The reaction solution was concentrated to dryness and the residue was dissolved in water (13 ml). The solution, which was adjusted the pH at 7.5 with the addition of 4 N aqueous sodium hydroxide solution, was adsorbed to Amberlite CG-50(NH4+) (6 ml). The resin was washed with water and then eluted with 0.3 N aqueous ammonia. The eluate was concentrated to dryness to yield 105 mg of 4'-deoxykanamycin A. This corresponds to an authentic sample of the compound disclosed in literature.

What we claim is:

1. 3',4'-Anhydro-4'-epi derivatives of kanamycin A of the formula:

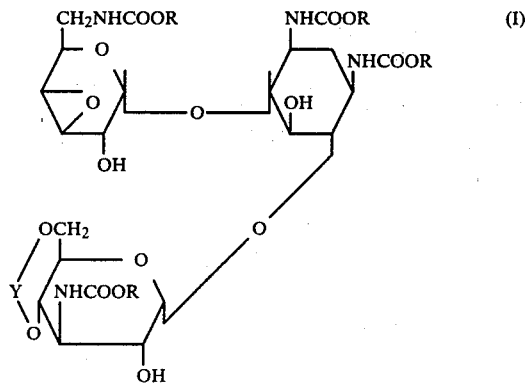

wherein R represents an alkyl of 1–4 carbon atoms, benzyl, phenyl or nitrophenyl, and Y represents an formylidene, ethylidene, isopropylidene, benzylidene, cyclopentylidene cyclohexylidene or tetrahydropyranylidene.

2. 3',4'-Anhydro-4'-epi-4'',6''-O-cyclohexylidene-tetra-N-t-butoxycarbonylkanamycin A.

3. A process for the preparation of 3',4'-anhydro-4'-epi-derivative of kanamycin A as claimed in claim 1, which comprises:

(a) reacting the tetra-N-protected, 4",6"-O-protected derivative of kanamycin A of formula (VIII)

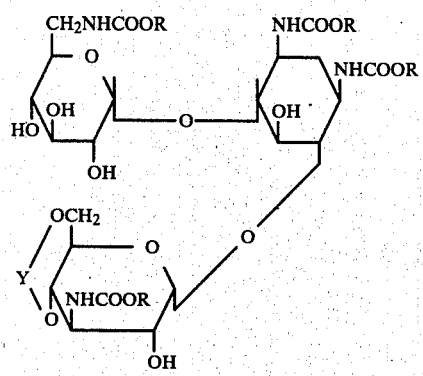

wherein R and Y are as defined in claim 1, with acetyl chloride or benzoyl chloride in pyridine at a temperature of 0° to 5° C. to preferentially acylate the 2'-, 3'- and 2"-hydroxyl groups of the protected kanamycin A derivative (VIII) and thereby produce the 2',3',2"-tri-O-acyl derivative of kanamycin A of the formula (IX)

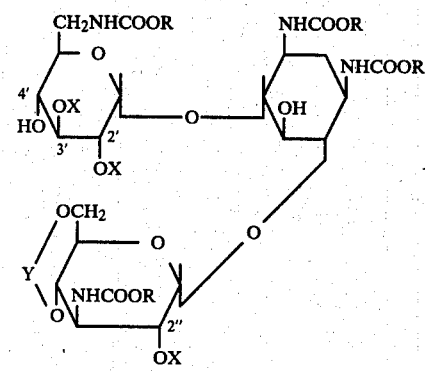

wherein R and Y are as defined above and X is acetyl or benzoyl, (b) reacting the compound of the formula (IX) with mesyl chloride, tosyl chloride or benzylsulfonyl chloride in pyridine at a temperature of 20° to 50° C. to prepare the 4'-O-sulfonylated derivative of kanamycin A of the formula (II)

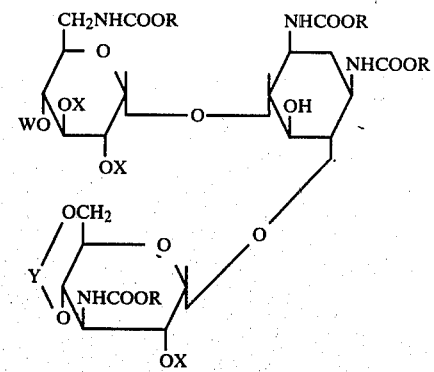

wherein R, Y and X are as defined above and W is mesyl, tosyl or benzylsulfonyl group, and (c) treating the 4'-O-sulfonyl derivative of kanamycin A of the formula (II) with an alkali metal methoxide or ethoxide in an alkanol of 1 to 4 carbon atoms at a temperature of 15° to 20° C. to produce the protected 3',4'-anhydro-4'-epi-kanamycin A derivative of the formula (I) as claimed in claim 1.

4. 3',4'-Anhydro-4'-epi derivatives of kanamycin A of the formula:

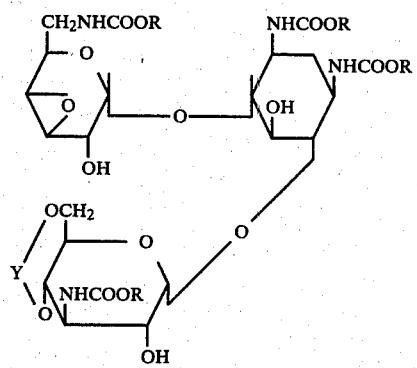

wherein R represents an alkyl of 1 to 4 carbon atoms and Y represents cyclohexylidene.

5. The compound of the formula (XI)

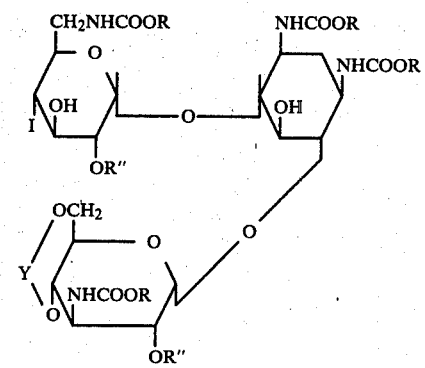

wherein R is an alkyl of 1 to 4 carbon atoms benzyl, phenyl or nitrophenyl, R" is benzoyl, and Y represents formylidene, ethylidene, isopropylidene, benzylidene, cyclopentylidene, cyclohexylidene or tetradropyranylidene.

6. 4'-Deoxy-4'-iodo-2',2"-di-O-benzoyl-4",6"-O-cyclohexylidene-tetra-N-t-butoxycarbonylkanamycin A.

* * * * *